(12) United States Patent
Close et al.

(10) Patent No.: US 10,617,576 B2
(45) Date of Patent: Apr. 14, 2020

(54) PROCESS FOR FORMING A FIBROUS NONWOVEN WEB WITH UNIFORM, DIRECTIONALLY-ORIENTED PROJECTIONS

(71) Applicant: Kimberly-Clark Worldwide, Inc., Neenah, WI (US)

(72) Inventors: Kenneth B. Close, New London, WI (US); Michael A. Schmidt, Alpharetta, GA (US); Jillian A. Walter, Atlanta, GA (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 16/253,884

(22) Filed: Jan. 22, 2019

(65) Prior Publication Data
US 2019/0151167 A1 May 23, 2019

Related U.S. Application Data

(60) Division of application No. 15/057,817, filed on Mar. 1, 2016, now abandoned, which is a continuation of
(Continued)

(51) Int. Cl.
*D01D 5/08* (2006.01)
*D01D 7/00* (2006.01)
(Continued)

(52) U.S. Cl.
CPC ............. *A61F 13/535* (2013.01); *D04H 1/56* (2013.01); *D04H 1/565* (2013.01); *D04H 1/74* (2013.01);
(Continued)

(58) Field of Classification Search
CPC ...... B29L 2031/726; D01D 5/08; D01D 7/04; D04H 1/56; D04H 1/565; D04H 1/70;
(Continued)

(56) References Cited

U.S. PATENT DOCUMENTS 3,034,180 A   5/1962   Bletzinger et al.
3,110,609 A   11/1963  Bletzinger
(Continued)

FOREIGN PATENT DOCUMENTS

EP   0604736 A2   7/1994
EP   0617940 A2   10/1994
(Continued)

*Primary Examiner* — Leo B Tentoni
(74) *Attorney, Agent, or Firm* — Craig M. bohlken

(57) ABSTRACT

A process and apparatus is used for making a fibrous nonwoven web with uniform, directionally-oriented projections by depositing fibrous material onto a first forming surface with holes positioned above a second forming surface with both forming surfaces traveling at different speeds to one another. As the fibers are deposited onto the first forming surface, a portion of the fibers are drawn down into the holes of the first forming surface forming the projections which contact the second forming surface. Due to the speed differential between the two forming surfaces the projections are uniformly skewed in the same direction. The resultant material is particularly suited for use as a wiping material which can be more abrasive in one direction but which is softer to the touch when wiped in the opposite direction thus making it a dual purpose material.

12 Claims, 4 Drawing Sheets

Related U.S. Application Data application No. 13/894,516, filed on May 15, 2013, now abandoned.

(60) Provisional application No. 61/649,742, filed on May 21, 2012.

(51) Int. Cl.
| | |
|---|---|
| *A61F 13/535* | (2006.01) |
| *D04H 1/74* | (2006.01) |
| *D04H 11/08* | (2006.01) |
| *D04H 1/56* | (2006.01) |
| *B29L 31/00* | (2006.01) |
| *A61F 13/53* | (2006.01) |

(52) U.S. Cl.
CPC .. *D04H 11/08* (2013.01); *A61F 2013/530233* (2013.01); *A61F 2013/530437* (2013.01); *B29L 2031/726* (2013.01); *Y10T 428/2395* (2015.04)

(58) Field of Classification Search
CPC .. D04H 1/72; D04H 1/74; D04H 3/02; D04H 3/03; D04H 3/16; D04H 5/06; D04H 5/08; D04H 11/08
USPC .......... 264/103, 167, 518, 555; 19/296, 299
See application file for complete search history.

(56) References Cited

U.S. PATENT DOCUMENTS

| | | | |
|---|---|---|---|
| 4,042,740 | A | 8/1977 | Krueger |
| 4,100,324 | A | 7/1978 | Anderson et al. |
| 4,103,058 | A | 7/1978 | Humlicek |
| 4,375,446 | A | 3/1983 | Fujii et al. |
| 4,408,638 | A | 10/1983 | Strom |
| 4,637,819 | A | 1/1987 | Ouellette et al. |
| 4,741,941 | A | 5/1988 | Englebert et al. |
| 4,854,984 | A | 8/1989 | Ball et al. |
| 5,098,519 | A | 3/1992 | Ramasubramanian et al. |
| 5,180,620 | A | 1/1993 | Mende |
| 5,213,881 | A | 5/1993 | Timmons et al. |
| 5,228,482 | A | 7/1993 | Fleischer |
| 5,242,632 | A | 9/1993 | Mende |
| 5,326,415 | A | 7/1994 | Thomas et al. |
| 5,332,613 | A | 7/1994 | Taylor et al. |
| 5,350,624 | A | 9/1994 | Georger et al. |
| 5,508,102 | A | 4/1996 | Georger et al. |
| 5,520,225 | A | 5/1996 | Quigley et al. |
| 5,565,255 | A | 10/1996 | Young et al. |
| 5,575,874 | A | 11/1996 | Griesbach et al. |
| 5,643,653 | A | 7/1997 | Griesbach et al. |
| 5,656,232 | A | 8/1997 | Takai et al. |
| 5,665,396 | A | 9/1997 | Ulman |
| 5,817,213 | A | 10/1998 | Ostermayer et al. |
| 5,853,628 | A | 12/1998 | Varona |
| 5,858,515 | A | 1/1999 | Stokes et al. |
| 5,871,607 | A | 2/1999 | Hamilton et al. |
| 5,962,112 | A | 10/1999 | Haynes et al. |
| 5,990,377 | A | 11/1999 | Chen et al. |
| 6,039,839 | A | 3/2000 | Trokhan et al. |
| 6,066,369 | A | 5/2000 | Schulz et al. |
| 6,141,833 | A * | 11/2000 | Sørensen ................ D04H 1/72 19/296 X |
| 6,228,216 | B1 | 5/2001 | Lindsay et al. |
| 6,264,872 | B1 | 7/2001 | Majors et al. |
| 6,395,957 | B1 | 5/2002 | Chen et al. |
| 6,610,173 | B1 | 8/2003 | Lindsay et al. |
| 6,660,362 | B1 | 12/2003 | Lindsay et al. |
| RE38,505 | E | 4/2004 | James et al. |
| 6,753,063 | B1 | 6/2004 | Pung et al. |
| 6,810,553 | B1 | 11/2004 | Otsuji et al. |
| 6,869,670 | B2 | 3/2005 | DeLucia et al. |
| 6,911,573 | B2 | 6/2005 | Chen et al. |
| 6,998,017 | B2 | 2/2006 | Lindsay et al. |
| 7,101,622 | B2 | 9/2006 | Chang et al. |
| 7,175,918 | B2 | 2/2007 | Saraf et al. |
| 7,176,150 | B2 | 2/2007 | Kopacz et al. |
| 7,300,554 | B2 | 11/2007 | LaFond et al. |
| 7,493,923 | B2 | 2/2009 | Barrett et al. |
| 8,043,984 | B2 | 10/2011 | Stadelman et al. |
| 2002/0132544 | A1 | 9/2002 | Takagaki |
| 2002/0155776 | A1 | 10/2002 | Mitchler et al. |
| 2003/0073367 | A1 | 4/2003 | Kopacz et al. |
| 2003/0077970 | A1 | 4/2003 | DeLucia et al. |
| 2003/0118777 | A1 | 6/2003 | Chang et al. |
| 2003/0200991 | A1 | 10/2003 | Keck et al. |
| 2003/0211802 | A1 | 11/2003 | Keck et al. |
| 2003/0213109 | A1 | 11/2003 | Neely et al. |
| 2004/0005457 | A1 | 1/2004 | DeLucia et al. |
| 2004/0127128 | A1 | 7/2004 | Thomas |
| 2004/0258844 | A1 | 12/2004 | Rivera et al. |
| 2004/0265534 | A1 | 12/2004 | Curro et al. |
| 2005/0067042 | A1 | 3/2005 | Hirota et al. |
| 2005/0148260 | A1 | 7/2005 | Kopacz et al. |
| 2005/0148261 | A1 | 7/2005 | Close et al. |
| 2005/0255297 | A1 | 11/2005 | Otsuka et al. |
| 2005/0260390 | A1 | 11/2005 | Croft et al. |
| 2006/0025031 | A1 | 2/2006 | Carter |
| 2006/0063456 | A1 | 3/2006 | Carter |
| 2006/0138693 | A1 | 6/2006 | Tuman et al. |
| 2006/0141881 | A1 | 6/2006 | Bergsten et al. |
| 2006/0169301 | A1 | 8/2006 | Haskett et al. |
| 2006/0246804 | A1 | 11/2006 | Thomas et al. |
| 2006/0266473 | A1 | 11/2006 | Senapati et al. |
| 2007/0028994 | A1 | 2/2007 | Kroll et al. |
| 2007/0028996 | A1 | 2/2007 | Quigley |
| 2007/0049153 | A1 | 3/2007 | Dunbar et al. |
| 2007/0065643 | A1 | 3/2007 | Kopacz et al. |
| 2007/0128411 | A1 | 6/2007 | Kawai et al. |
| 2007/0129230 | A1 | 6/2007 | Sosalla |
| 2007/0130713 | A1 | 6/2007 | Chen et al. |
| 2007/0190878 | A1 | 8/2007 | Willman et al. |
| 2007/0197117 | A1 | 8/2007 | Austin et al. |
| 2007/0251851 | A1 | 11/2007 | Warren et al. |
| 2008/0119103 | A1 | 5/2008 | Ng et al. |
| 2008/0177242 | A1 | 7/2008 | Chang et al. |
| 2009/0065166 | A1 | 3/2009 | Quigley |
| 2009/0065167 | A1 | 3/2009 | Quigley |
| 2009/0068909 | A1 | 3/2009 | Quigley |
| 2009/0078388 | A1 | 3/2009 | Barrett |
| 2009/0108504 | A1 | 4/2009 | Slama et al. |
| 2009/0111347 | A1 | 4/2009 | Peng et al. |
| 2009/0118690 | A1 | 5/2009 | Cohen et al. |
| 2009/0233049 | A1 | 9/2009 | Jackson et al. |
| 2009/0233072 | A1 | 9/2009 | Harvey et al. |
| 2013/0309439 | A1 | 11/2013 | Close et al. |
| 2016/0175170 | A1 | 6/2016 | Close et al. |

FOREIGN PATENT DOCUMENTS

| | | |
|---|---|---|
| EP | 0843042 A1 | 5/1998 |
| EP | 0750063 B1 | 10/1999 |
| EP | 1241288 A2 | 9/2002 |
| EP | 1350456 A1 | 10/2003 |
| JP | 11286863 A | 10/1999 |
| JP | 2004121701 A | 4/2004 |
| JP | 2005145020 A | 6/2005 |
| JP | 2006002303 A | 1/2006 |
| JP | 2008025079 A | 2/2008 |
| WO | 2003031172 A1 | 4/2003 |
| WO | 2005013873 A1 | 2/2005 |
| WO | 2005111282 A1 | 11/2005 |
| WO | 2007024447 A1 | 3/2007 |
| WO | 2008073101 A1 | 6/2008 |

* cited by examiner

PROCESS FOR FORMING A FIBROUS NONWOVEN WEB WITH UNIFORM, DIRECTIONALLY-ORIENTED PROJECTIONS

The present application is a divisional application of and claims priority to U.S. patent application Ser. No. 15/057817, filed on Mar. 1, 2016, abandoned, which is a continuation of U.S. patent application Ser. No. 13/894516, filed on May 15, 2013, abandoned, which claims priority to U.S. Patent Application No. 61/649742, filed on May 21, 2012, expired, the contents of which are all incorporated herein by reference.

BACKGROUND OF THE INVENTION

The present invention is directed to fibrous nonwoven webs with uniform, directionally-oriented projections located on at least one surface of the formed material as well as the process and apparatus for making such a material.

Disposable products are an ever increasing portion of the consumer market, especially in the context of personal products such as cleaning products for the face and body. The same is true for products used for household cleaning and other cleaning applications. A commonly desired attribute for all such products is the cleaning ability of the product and its ability to absorb and retain fluids. Today there are many wiping products that are available in either a dry or wet state. A large number of such products are relatively flat, two-dimensional products with little variability in the topography of the material. Other materials are textured due to embossing of the wiping material. Still other materials are tufted. See, for example, U.S. Patent Application No. 2003/0211802 to Keck et al. assigned to Kimberly-Clark Worldwide, Inc. which discloses three-dimensional coform nonwoven coform webs which have projections which increase the bulk of the nonwoven web and aid in the scrubbing and cleaning ability of the coform web. See also U.S. Pat. No. 5,180,620 to Mende assigned to Mitsui Petrochemical Industries, Ltd. which discloses a nonwoven fabric comprised of meltblown fibers with projections extending from the fabric base. Still a further example is U.S. Patent Application No. 2007/0130713 to Chen et al. and assigned to Kimberly-Clark Worldwide, Inc. which discloses a cleaning wipe with a textured surface which may be used as a stand-alone product or can be incorporated into a cleaning tool. The wipe includes a base material having an application face and a plurality of projections extending generally transversely from the application face. The projections may have various shapes, including a mushroom shape. A high friction element can be applied to at least a portion of the projections to provide enhanced abrasive scrubbing functionality. With the mushroom-shaped embodiment the projections have a cross-sectional shape such that the head portion extends laterally beyond and overhangs the base portion. The voids or spaces between the projections are said to be particularly well suited for trapping hair and other difficult to retain materials from the surface being cleaned. The tapered voids (tapered from the head portion of the projections towards the land areas) allow for hair and other relatively larger particulate matter to become essentially "wedged" into the void spaces, with the tapered profile of the projections serving to "lock" the particulate matter within the voids. Yet another example of a material with a three-dimensional shape is disclosed in U.S. Patent Application No. 2002/0132544 to Takagaki assigned to Toyoda Boshoku Corporation which spins semi-molten fibers onto a mold. U.S. Pat. No. 6,610,173 to Lindsay et al. assigned to Kimberly-Clark Worldwide, Inc. discloses a method for imprinting a paper web during a wet pressing event with asymmetrical protrusions corresponding to the deflection conduits of a deflection member. In certain embodiments, if substantial shear is applied to the deflection members by way of differential velocity transfer, a snowplow effect can be produced in which the moist fibers are sheared and piled up toward one side of the protrusion.

Despite the foregoing examples of products and processes for creating such textured materials, there is still a need for materials that are textured and easy to produce. The present invention is directed to a material which has protrusions which are directionally-oriented in one direction in a uniform manner. In so doing, the projections can act to provide more friction when wiped across a surface in one direction than in another. As a result, the material will have a somewhat rougher feel when wiped in one direction and a smoother feel in the opposite direction. Also disclosed is a process and apparatus for making such a material.

DEFINITIONS

As used herein, the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, which is hereby incorporated by reference in its entirety. Meltblown fibers are microfibers, which may be continuous or discontinuous, and are generally smaller than 10 microns in average diameter. The term "meltblown" is also intended to cover other processes in which a high velocity gas (generally air) is used to aid in the formation of the filaments, such as melt spraying or centrifugal spinning.

As used herein, the term "coform nonwoven web" or "coform material" means composite materials comprising a mixture or stabilized matrix of thermoplastic filaments and at least one additional material, usually called the "second material" or the "secondary material". As an example, coform materials may be made by a process in which at least one meltblown die head is arranged near a chute through which the second material is added to the web while it is forming. The second material may be, for example, an absorbent material such as fibrous organic materials such as woody and non-wood pulp such as cotton, rayon, recycled paper, pulp fluff; superabsorbent materials such as superabsorbent particles and fibers; inorganic absorbent materials and treated polymeric staple fibers and the like; or a non-absorbent material, such as non-absorbent staple fibers or non-absorbent particles. Exemplary coform materials are disclosed in commonly assigned U.S. Pat. No. 5,350,624 to Georger et al.; U.S. Pat. No. 4,100,324 to Anderson et al.; and U.S. Pat. No. 4,818,464 to Lau et al.; the entire contents of each is hereby incorporated by reference in their entirety for all purposes.

As used herein the term "spunbond fibers" refers to small diameter fibers of molecularly oriented polymeric material. Spunbond fibers may be formed by extruding molten thermoplastic material as filaments from a plurality of fine, usually circular capillaries of a spinneret with the diameter of the extruded filaments then being rapidly reduced as in, for example, U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al, and U.S. Pat. No. 5,382,400 to Pike et al. which are incorporated by reference in their entirety for all purposes. Spunbond fibers are generally not tacky when they are deposited onto a collecting surface and are generally continuous. Spunbond fibers are often about 10 microns or greater in diameter. However, fine fiber spunbond webs (having and average fiber diameter less than about 10 microns) may be achieved by various methods including, but not limited to, those described in commonly assigned U.S. Pat. No. 6,200,669 to Mormon et al. and U.S. Pat. No. 5,759,926 to Pike et al.

SUMMARY OF THE INVENTION

The present invention is directed to a process for forming a fibrous nonwoven web with uniform, directionally-oriented projections. The process involves providing a first forming surface defining a plurality of openings therein and providing a second forming surface which is pervious to air. The first forming surface is overlaid atop the second forming surface and the first forming surface is caused to travel in a first direction at a first speed and the second forming surface is caused to travel in the first direction at a second speed to cause a speed differential between the first forming surface and the second forming surface. A plurality of fibers are deposited onto the first forming surface to form a fibrous nonwoven web while causing a portion of the plurality of fibers to extend through the openings in the first forming surface and then contact the second forming surface to form a plurality of fibrous projections in the fibrous nonwoven web. The speed differential between the first and second forming surfaces causes the projections to have a uniform, directional orientation relative to the first direction of travel of the first forming surface and once the projections are formed and oriented the fibrous nonwoven web with the uniform, directionally-oriented projections is removed from the first forming surface. If desired, the process can be modified by providing a vacuum source beneath the second forming surface on a side of the second forming surface opposite the first forming surface to aid in a movement of the fibers through the openings in the first forming surface and contact the second forming surface.

As a result of the speed differential between the first and second forming surfaces, one of the first and second forming surfaces can be caused to travel a differential distance "y" as defined herein which is between about two and about six inches (about 5.1 and about 15.2 centimeters) further than the other of the first and second forming surfaces travels over the same amount of time in a prescribed distance "D1" from when the material forming the fibrous nonwoven web is laid down onto the first forming surface at a first location and a second location when the heads of the formed projections are no longer in contact with the second forming surface. It is this difference in distance traveled due to the speed differential of the first and second forming surfaces between the first and second locations that causes the uniform, directional orientation of the projections of the so-formed fibrous nonwoven web.

To create the speed differential between the two forming surfaces, the process can involve driving one of the first and second forming surfaces by frictional engagement with the other of the first and second forming surfaces. Alternatively, the process can involve driving the first forming surface in the first direction independently of the second forming surface by having each of the forming surfaces driven by their own separate drive devices.

An apparatus for forming a fibrous nonwoven web with uniform, directionally-oriented projections can include a first forming surface defining a plurality of openings therein with the first forming surface being capable of moving in a first direction at a first speed along with a second forming surface which is pervious to air and capable of moving in a first direction at a second speed with the second forming surface being positioned below the first forming surface and the second speed being different than the first speed. The apparatus includes a fiber deposition apparatus positioned above and distanced from a surface of the first forming surface opposite the second forming surface and a vacuum assist apparatus positioned below the second forming surface on a side of the second forming surface opposite the first forming surface. In certain applications, a coform apparatus can be used as the fiber deposition apparatus.

In one embodiment of the apparatus the first forming surface and the second forming surface can be frictionally engaged with one another with one of the first and second forming surfaces being driven by the other of the first and second forming surfaces due to the frictional engagement between the first and second forming surfaces. In an alternate embodiment of the apparatus, the first and second forming surfaces can be driven in the first direction separately from one another by separate drive devices.

The first forming surface if desired can comprise a flexible belt defining a plurality of holes therein and extending there through which are spaced apart by a land area in the belt with it being preferable that the land area is impervious to air emanating from the fiber deposition apparatus.

Also disclosed herein is a fibrous nonwoven web having a top surface, an opposed bottom surface, a length, a width and a thickness with a plurality of uniform, directionally-oriented projections emanating from the top surface of the web. The fibrous nonwoven web, because of the uniform directional orientation of the projections, has a knap on the top surface of the web which is smoother to the touch when engaged in one direction as opposed to the opposite direction. The projections each have a base portion with a vertical axis generally perpendicular to a plane formed by the top surface of the web and a head portion connected to the base portion. This vertical axis is located at a position in the base portion such that at least a portion of the base portion has a lateral dimension that is equally spaced on either side of the vertical axis. The head portion of the projection is asymmetrically located relative to the base portion and the vertical axis such that the head portion has a lateral dimension which is skewed with respect to the vertical axis so that more of the head portion is located on one side of said vertical axis than the base portion when viewing the head portion and the base portion from the same position. In addition, the head portion can form an overhang area with respect to said base portion.

The fibrous nonwoven web disclosed herein can be used in a wide variety of products including a wipe and other cleaning products. It can also be used as a personal care absorbent article wherein as least a portion of the article comprises the disclosed fibrous nonwoven web. Such personal care absorbent articles typically comprise a body side liner and a garment-facing sheet with an absorbent core disposed between the body side liner and the garment facing sheet. In such products it is desirable that the body side liner comprise the fibrous nonwoven web disclosed herein. Such personal care absorbent articles can be selected from the group consisting of a diaper, a sanitary napkin, a child training pant and an adult incontinence device.

BRIEF DESCRIPTION OF THE FIGURES

A full and enabling disclosure of the present invention, including the best mode thereof to one skilled in the art, is set forth more particularly in the remainder of the specification, which includes reference to the accompanying figures, in which.

DETAILED DESCRIPTION OF THE INVENTION

Product Description

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. When ranges for parameters are given, it is intended that each of the endpoints of the range are also included within the given range. It is to be understood by one of ordinary skill in the art that the present discussion is a description of exemplary embodiments only, and is not intended as limiting the broader aspects of the present invention, which broader aspects are embodied exemplary constructions.

Figure 1:
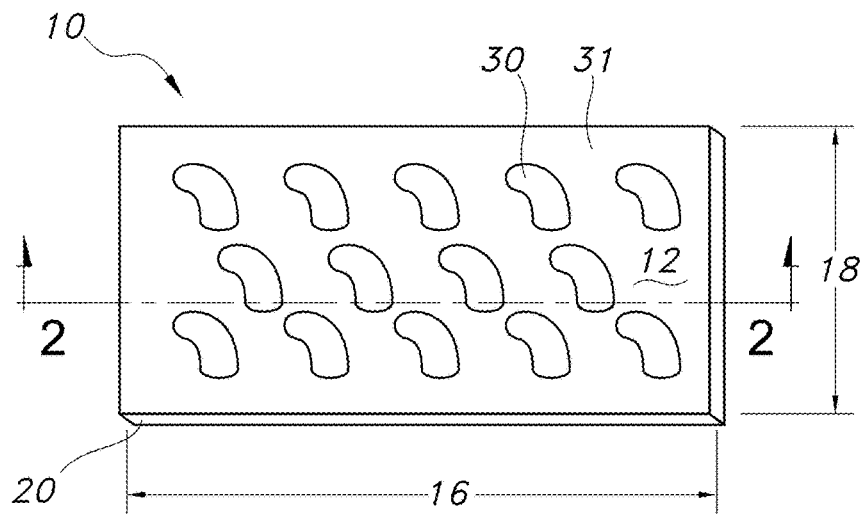
FIG. 1 is a perspective view of one embodiment of a fibrous nonwoven web with uniform, directionally-oriented projections according to the present invention.
Figure 2:
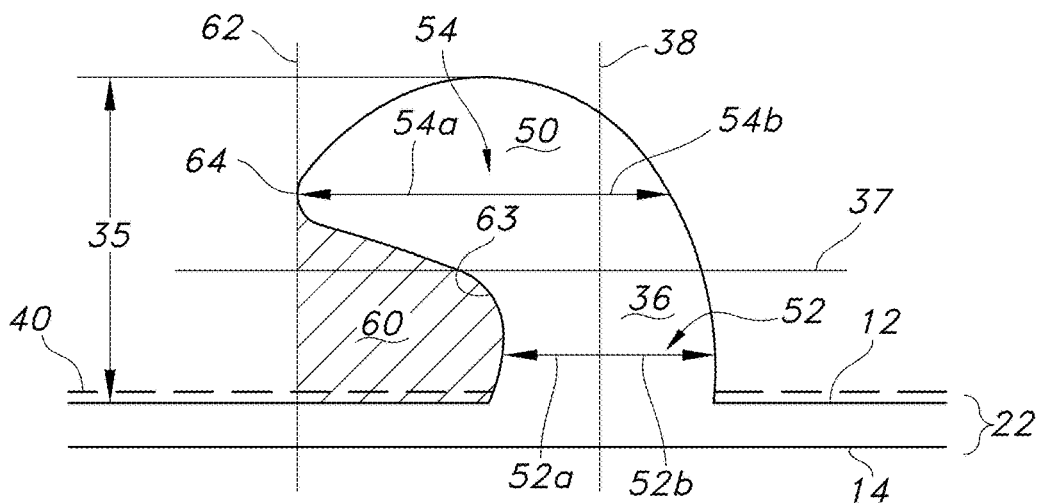
FIG. 2 is a cross-section of the material shown in FIG. 1 taken along line 2-2 of FIG. 1 showing a single oriented projection according to the present invention.

Turning to FIGS. 1 and 2 there is shown a fibrous nonwoven web 10 with uniform, directionally-oriented projections according to the present invention. The web 10 has a top surface 12 an opposed bottom surface 14, a length 16, a width 18 and a thickness 20.

Emanating from the top surface 12 is a plurality of projections 30 which are uniformly oriented in the same direction and separated by land area 31. The projections 30 have a base portion 36 which defines a vertical axis 38 which is generally perpendicular to a plane 40 defined by the top surface 12 of the web 10.

The projections 30 have a head portion 50 connected to the based portion 36. The projections 30 have an overall height 35 as measured from the top surface 12 of the web 10 to the top of the head portion 50 of the projection 30. This distance 35 can be divided by a line 37 which is generally parallel to the top surface 12 and the plane 40. The portion of the projection 30 above this line 37 is considered the head portion 50 and the portion of the projection 30 below this line 37 is considered the base portion 36. Generally, this line 37 will be drawn at a point that is below the main overhanging portion of the head portion 50 and thus below the point where the line 62 contacts the head 50. See FIG. 2.

The vertical axis 38 is located at a position in the base portion 36 such that the base portion 36 has a lateral dimension 52 that is equally spaced on either side of the vertical axis 38 when the projection is viewed from a side such as is shown in FIG. 2. By "equally spaced" it is meant that the vertical axis 38 can be positioned such that the lateral dimension 52 (which is determined below the line 37) can be divided into a left portion 52a and a right portion 52b and the dimensions of these two portions (52a and 52b) are within plus or minus 10 percent of one another.

In contrast, the head portion 50 of the projection 30 has a lateral dimension 54 which is located above the line 37 and which has a left portion 54a and a right portion 54b relative to the vertical axis 38. As can be seen from FIG. 2, the head portion 50 is asymmetrically located with respect to the vertical axis 38 and the base portion 36 such that the head portion 50 is skewed with respect to the vertical axis 38 with more of the lateral dimension 54 being located on one side (in this case 54a) of the vertical axis 38 than the other side (in this case 54b) when viewing the lateral dimensions 52 and 54 from the same position.

As a result of this vertical skewing of the projections 36, there is created an overhang area 60 such as is shown in FIG. 2. This overhang area 60 can be seen when viewing the projections 36 from the side. In FIG. 2, the overhang area 60 is defined by drawing a vertical line 62 which is tangent to a portion of the head portion 50 (the overhanging edge 64), which does not intersect a portion of the head portion 50, and which is also generally parallel to the vertical axis 38.

The overhand area 60 is bounded by the line 62, the side 63 of the projection 30 and if need be the top surface 12 of the web 10.

Figure 3:
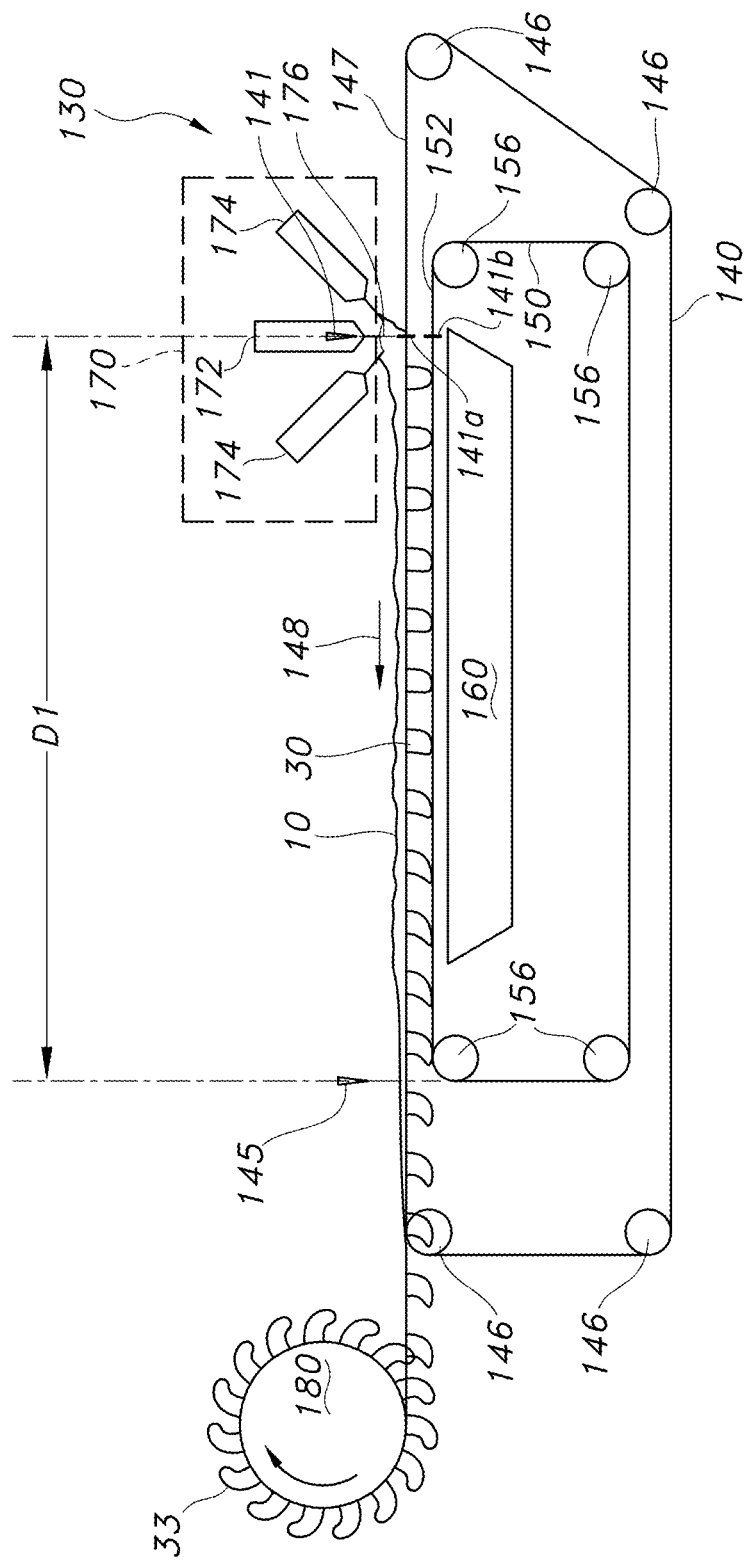
FIG. 3 is a schematic side view of a process and apparatus according to the present invention for forming a fibrous nonwoven web with uniform, directionally-oriented projections according to the present invention.

Due to the nature of the equipment and process by which the web 10 is made, the overhang areas 60 will be created in a direction which is generally parallel to the machine direction (MD) in which the web 10 is made in the process and apparatus such as is shown in FIG. 3 of the drawings. As explained in more detail below, depending on the relative speed of the two forming surfaces used to form the projections 30, the overhang areas 60 and the skewing of the head portions 50 will be parallel to the machine direction movement 148 and formation of the web 10. If the first forming surface 140 of the apparatus 130 is moving faster that the second forming surface 150, the overhanging edge 64 will point in the opposite direction of the machine direction 148 of the apparatus 130 in FIG. 3. Conversely, if the first forming surface 140 of the apparatus 130 is moving slower that the second forming surface 150, the overhanging edge 64 will point in the same direction as the machine direction 148 of the apparatus 130 in FIG. 3. Thus, when it is said that the direction of the orientation of the projections 30 is "uniform" it is meant that in a measured area of the top surface 12 of the web 10, at least 70 percent of the projections 30 are slanted to the same side of the vertical axis 38.

The web 10 can be made from a variety of materials including meltblown materials, coform materials, air-laid materials, bonded-carded web materials, hydroentangled materials, spunbond materials and the like, and can comprise synthetic or natural fibers. A preferred material is a coform web.

The fibrous nonwoven web 10 may be used as a wet wipe, and in particular baby wipes. Different physical characteristics of the fibrous nonwoven web may be varied to provide the best quality wet wipe. For example, formation, diameter of meltblown fibers, the amount of lint, opacity and other physical characteristics of the fibrous nonwoven web may be altered to provide a useful wet wipe for consumers.

Typically, the fibrous nonwoven web 10 is a combination of meltblown fibrous materials and secondary fibrous materials. The relative percentages of the meltblown fibrous materials and secondary fibrous materials in the web can vary over a wide range depending on the desired characteristics of the fibrous nonwoven web. For example, fibrous nonwoven webs can have from about 20 to about 60 weight percent (wt. %) of meltblown fibrous materials and from about 40 to 80 wt. % of secondary fibers. Desirably, the weight ratio of meltblown fibrous materials to secondary fibers can be from about 20/80 to about 60/40. More desirably, the weight ratio of meltblown fibrous materials fibers to secondary fibers can be from about 25/75 to about 40/60.

Generally speaking, the overall basis weight of the fibrous nonwoven web 10 is from about 10 grams per square meter (gsm) to about 500 gsm, and more particularly from about 17 gsm to about 200 gsm, and still more particularly from about 25 gsm to about 150 gsm. The basis weight of the fibrous nonwoven web may also vary depending upon the desired end use. For example, a suitable fibrous nonwoven web for wiping the skin may define a basis weight of from about 30 to about 80 gsm and desirably about 45 to about 75 gsm. The basis weight (in grams per square meter, g/m2 or gsm) is calculated by dividing the dry weight (in grams) by the area (in square meters).

One approach in making the fibrous nonwoven web 10 is to mix meltblown fibrous materials with one or more types of secondary fibrous materials and/or particulates. The mixture is collected in the form of fibrous nonwoven web which may be bonded or treated to provide a coherent nonwoven material that can take advantage of at least some of the properties of each component. These mixtures are referred to as "coform" materials because they are formed by combining two or more materials in the forming step into a single structure.

Meltblown fibrous materials suitable for use in the fibrous nonwoven web include polyolefins, for example, polyethylene, polypropylene, polybutylene and the like, polyamides, olefin copolymers and polyesters. In accordance with a particularly desirable embodiment, the meltblown fibrous materials used in the formation of the fibrous nonwoven web are polypropylene. See for example WO 2011/034523 for additional information on suitable polymers for the meltblown fibers which is incorporated herein for all purposes in its entirety.

The fibrous nonwoven web also includes one or more types of secondary fibrous materials to form the nonwoven web. Any secondary fibrous material may generally be employed in the coform nonwoven structure, such as absorbent fibers, particles, etc. In one embodiment, the secondary fibrous material includes fibers formed by a variety of pulping processes, such as kraft pulp, sulfite pulp, thermo-mechanical pulp, etc. The pulp fibers may include softwood fibers having an average fiber length of greater than 1 millimeter (mm) and particularly from about 2 to about 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable include those available from Weyerhaeuser Co. of Federal Way, Wash. under the designation "Weyco CF-405." Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used, such as abaca, sabai grass, milkweed floss, pineapple leaf, and so forth. In addition, in some instances, synthetic fibers can also be utilized. Wood pulp fibers are particularly preferred as a secondary fibrous material because of low cost, high absorbency and retention of satisfactory tactile properties.

Besides or in conjunction with pulp fibers, the secondary fibrous material may also include a superabsorbent that is in the form of fibers, particles, gels, etc. Generally speaking, superabsorbents are water-swellable materials capable of absorbing at least about 20 times its weight and, in some cases, at least about 30 times its weight in an aqueous solution containing 0.9 wt. % sodium chloride. The superabsorbent may be formed from natural, synthetic and modified natural polymers and materials. Examples of synthetic superabsorbent polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly (vinyl pyrrolidone), poly(vinylmorpholinone), poly(vinyl alcohol), and mixtures and copolymers thereof. Further, superabsorbents include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful. Particularly suitable superabsorbent polymers are HYSORB 8800AD (BASF of Charlotte, N.C. and FAVOR SXM 9300 (available from Evonik Stockhausen of Greensboro, N.C.).

The secondary fibrous materials are interconnected by and held captive within the microfibers by mechanical entanglement of the microfibers with the secondary fibrous materials, the mechanical entanglement and interconnection of the microfibers and secondary fibrous materials forming a coherent integrated fiber structure. The coherent integrated fiber structure may be formed by the microfibers and secondary fibrous materials without any adhesive, molecular or hydrogen bonds between the two different types of fibers. The material is formed by initially forming a primary air stream containing the meltblown microfibers, forming a secondary air stream containing the secondary fibrous materials, merging the primary and secondary streams under turbulent conditions to form an integrated air stream containing a thorough mixture of the microfibers and secondary fibrous materials, and then directing the integrated air stream onto a forming surface to air form the fabric-like material. The microfibers are in a soft nascent condition at an elevated temperature when they are turbulently mixed with the pulp fibers in air.

In certain embodiments the web 10 may be used as a "wet" or "premoistened" wipe in that it contains a liquid solution for cleaning, disinfecting, sanitizing, etc. The particular liquid solutions are not critical and are described in more detail in U.S. Pat. No. 6,440,437 to Krzysik et al.; U.S. Pat. No. 6,028,018 to Amundson et al.; U.S. Pat. No. 5,888,524 to Cole; U.S. Pat. No. 5,667,635 to Win et al.; and U.S. Pat. No. 5,540,332 to Kopacz et al., which are incorporated herein in their entirety by reference thereto for all purposes. The amount of the liquid solution employed may depend upon the type of wipe material utilized, the type of container used to store the wipes, the nature of the cleaning formulation, and the desired end use of the wipes. Generally, each wipe contains from about 150 to about 600 wt. % and desirably from about 300 to about 500 wt. % of a liquid solution based on the dry weight of the nonwoven structure.

Process and Apparatus Description

Figure 4:
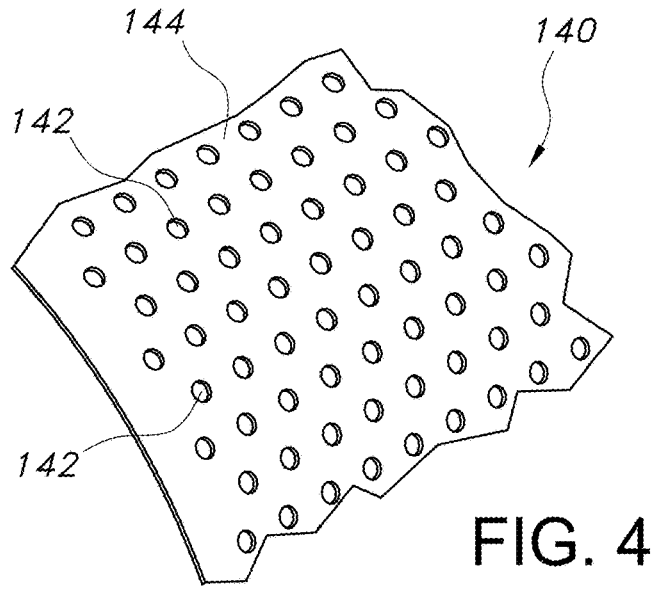
FIG. 4 is a perspective view of a representative portion of a first forming surface of an apparatus according to the present invention.

Turning to FIG. 3 of the drawings there is shown a process and apparatus 130 for forming a fibrous nonwoven web 10 with directionally oriented projections 30 according to the present invention. The apparatus 130 includes a first forming surface 140 and a second forming surface 150. The first forming surface 140 is positioned above or atop the second forming surface 150 in the area where web formation takes place. In FIG. 3, the first forming surface 140 is a flexible mat or belt with a plurality of apertures or holes 142 defined therein as also shown in the partial view of the first forming surface 140 shown in FIG. 4. While the land areas 144 of the surface 140 can be air permeable or impermeable, it is desirable that the land areas 144 not be permeable to air to increase the suction effect through the holes 142 caused by the vacuum assist 160 positioned below the first and second forming surfaces (140 and 150).

Rubberized mats or endless belts have been found to work particularly well as the first forming surface 140. Such mats are available from F.N. Sheppard and Company of Erlanger, Ky. They are vulcanized endless belts treated with release coatings. The belt material must be chosen to be heat resistant and compatible with the polymers being used. For polyolefin fibers, urethane coatings work well. Belt thicknesses typically range between about 1.6 and about 5.9 millimeters (mm). The holes in the belt used for the below examples had a staggered pattern of circular holes having a 0.25 inch (6.35 mm) diameter with a center-to-center spacing between holes in each row of 0.38 inches (9.65 mm). Staggered length between rows was 0.19 inches (4.83 mm) as measured from edge-to-edge. To facilitate processing, the belt had an unperforated border on its side edges of approximately 2.63 inches (66.8 mm). While the holes used for the below examples were circular, other shapes can also be used. It should be appreciated that the foregoing description is of one particular embodiment of a forming surface 140. Other materials and dimensions can be used depending upon the particular parameters desired in the web material 10 and projections 30. For example, if projections 30 with greater overall heights 35 are desired, thicker belt materials may be used. In addition, the spacing of the holes 142 and the shape of the holes 142 may be varied depending on the end needs of the web 10.

The first forming surface 140 is driven by a conventional drive assembly which for sake of simplicity is shown by one or more drive rolls 146 in FIG. 3. The drive rolls 146 cause the first forming surface 140 to travel in a first direction 148 shown by arrow 148 in FIG. 3 at a first speed. Such drive systems are well known to those of ordinary skill in the art.

The second forming surface 150 is positioned below the first forming surface 140 and is air permeable so as to enable the vacuum assist apparatus 160 to draw the fibers of the fibrous nonwoven web 10 down into the holes 142 and at least partially contact the top surface 152 of the second forming surface 150. It is desirable that the second forming surface 150 be driven by its own drive assembly which for sake of simplicity is shown by one or more drive rolls 156. The drive roll or rolls 156 causes the second forming surface to travel in the same first direction 148 but at a second speed which causes a speed differential to be created between the first forming surface 140 and the second forming surface 150. Again, such drive systems are well known to those of ordinary skill in the art.

Typically the second forming surface 150 is a woven wire mesh structure such as is available from Albany International Company of Rochester, N.H. The spacing of the wires in the wire mesh can be varied but the wire mesh must be sufficiently open so as to allow a sufficient vacuum to be pulled by the vacuum assist apparatus 160. Exemplary of these wire weave geometry forming surfaces is the forming wire FORMTECH™ 6 manufactured by Albany International Co. of Rochester, N.H. Such a wire has a "mesh count" of about six strands by six strands per square inch (about 2.4 by 2.4 strands per square centimeter) resulting in about 36 foramina or "holes" per square inch (about 5.6 per square centimeter). The FORMTECH™ 6 wire is made from polyester and has a warp diameter of about 1 millimeter, a shute diameter of about 1.07 millimeters, a nominal air permeability of approximately 41.8 m3/min (1475 ft3/min), a nominal caliper of about 0.2 centimeters (0.08 inch) and an open area of approximately 51%. Another exemplary forming surface available from the Albany International Co. is the forming wire FORMTECH™ 10, which has a mesh count of about 10 strands by 10 strands per square inch (about 4 by 4 strands per square centimeter) resulting in about 100 foramina or "holes" per square inch (about 15.5 per square centimeter). Still another suitable forming wire is FORMTECH™ 8, which has an open area of 47% and is also available from Albany International Co. Of course, other forming wires and surfaces (e.g., drums, plates, etc.) may be employed. Also, surface variations may include, but are not limited to, alternate weave patterns, alternate strand dimensions, release coatings (e.g., silicones, fluorochemicals, etc.), static dissipation treatments, and the like. Still other suitable foraminous surfaces that may be employed are described in U.S. Patent Application Publication No. 2007/0049153 to Dunbar et al. which is incorporated herein by reference thereto for all purposes.

As stated previously, the fibrous nonwoven web 10 can be formed from any number of fibrous structures such as coform materials, carded staple fibers, meltblown webs, spun bond webs and other fibrous web forming processes. The key aspect is that the fibers on the top surface 147 of the first forming surface 140 are capable of being drawn down into the holes 142 such that they come in contact with the top surface 152 of the second forming surface 150 so that the speed differential between the two forming surfaces can cause the projections 30 to skew and take on a uniform directional orientation relative to the first direction of movement 148 of the first forming surface 140.

In FIG. 3, the fibrous nonwoven web 10 is formed from a coform material which is a mixture of meltblown fibers and wood pulp fibers. The forming apparatus 170, which in this case is a coform apparatus 170, includes a central source 172 of pulp fibers and two meltblown dies 174 which together create meltblown fibers which mix with the pulp fibers to form a coform mix 176 which is deposited down onto the top surface 147 of the first forming surface 140. As the first forming surface 140 moves in the first direction 148 at its first speed, the coform mix 176 encounters the vacuum 160 which, along with the force of deposition, causes a portion of the coform fiber mix 176 to be drawn down into the apertures 142 in the first forming surface 140 to form the projections 30. Due to the fact that the first forming surface 140 is positioned atop of the second forming surface 150, the fibers of the projections 30 coming through the apertures 142 in the first forming surface 140 contact the top surface 152 of the second forming surface 150 but are prevented from being drawn down into the vacuum 160. It should be noted that other configurations of meltblown and secondary fiber feeds also may be used as well as multiple banks of coform or other fibrous structures, especially when higher line speeds or higher basis weights are being used. Some examples of such coform techniques are disclosed in U.S. Pat. No. 4,100,324 to Anderson et al.; U.S. Pat. No. 5,350,624 to Georger et al.; and U.S. Pat. No. 5,508,102 to Georger et al., as well as U.S. Patent Application Publication Nos. 2003/0200991 to Keck et al. and 2007/0049153 to Dunbar et al., all of which are incorporated herein in their entirety by reference thereto for all purposes.

As a result of the speed differential between the two forming surfaces (140 and 150) and the frictional engagement of the fibers of the projections 30 in contact with the second forming surface 150, the symmetrically-formed projections 30 begin to uniformly skew in the same direction. In the embodiment of FIG. 3, the first speed of the first forming surface 140 is slower than the second speed of the second forming surface 150. Consequently, the head portions 50 of the projections 30 are skewed forward to form leading hooks 33 as are shown schematically on the left side of the process in FIG. 3 as the resultant fibrous nonwoven web 10 is wound up on take-up roll 180. Alternatively, if the speed differential is such that the second speed of the second forming surface 150 is slower than that of the first speed of the first forming surface 140, the projections 30 in the fibrous web 10 will skew in the opposite direction (that is, opposite of the direction of arrow 148 in FIG. 3) as the web 10 is wound up on take-up roll 180. In either speed configuration, the degree of directional bending of the projections 30 can be controlled in part by way of the speed differential between the two forming surfaces (140 and 150).

In the embodiment of the process and apparatus shown in FIG. 3 of the drawings, the first forming surface 140 and the second forming surface 150 are each driven independently of one another so the separate drive systems can be separately controlled to vary the speed differential and thus the amount of skewing or orienting of the projections 30 in the web 10. An alternate embodiment, not shown, is to drive one of the two forming surfaces and not the other (140 or 150) and allow the two forming surfaces to contact one another such that the frictional engagement of the two forming surfaces drives the other surface. It has been found that there is enough friction between the two surfaces to drive the non-driven one but there is also enough slip to cause the non-driven surface to travel at a different speed than the driven surface thereby creating the same effect needed to skew or orient the projections 30 in the web 10. In this regard, it was generally found that driving the second forming surface 150 and not driving the first forming surface 140 worked best. In addition, by adjusting the rollers 146 and 156, the amount of gap, if any, and thus the frictional engagement of the two surfaces (140 and 150) can be adjusted to control the amount of engagement and drag between the two surfaces.

The line speeds of the two forming surfaces (140 and 150) will vary depending upon the materials being used to form the fibrous web 10, the basis weight needed, the amount of vacuum being used and other parameters commonly associated with forming such webs including coform webs. For the basis weights described herein, generally the line speeds will range between about 30 meters per minute (100 feet per minute) and about 600 meters per minute (2,000 feet per minute), desirably between about 90 meters per minute (300 feet per minute) and about 378 meters per minute (1240 feet per minute) and more desirably between about 198 meters per minute (650 feet per minute) and about 304 meters per minute (1000 feet per minute).

The meltblown fibers used in the coform process assist in maintaining the orientation of the projections 30 once the web 10 is formed. It is believed that because the meltblown fibers crystallize at a relatively slow rate, they are soft upon deposition onto the first and second forming surfaces (140 and 150). Thus the speed differential between the first and second forming surfaces creates a drag on the head portion 50 of the projections 30 which, by the time the web 10 is removed from the forming surfaces, has set in the oriented formation. After the fibers crystallize, they are then able to hold the shape and maintain the orientation.

The degree of orientation can be varied by varying the amount of the speed differential between the first and second forming surfaces (140 and 150) and thus the amount of distance that one forming surface covers versus the other in the prescribed amount of time it takes the first forming surface 140 to travel the distance between the first location 141 and the second location 145 denoted as "D1" in FIG. 3. In the context of distance traveled, to form the projections 30, it is desirable to cause one of the first 140 and second 150 forming surfaces to travel a distance "y" as defined herein which is between about 2 inches (51 mm) and about six inches (152 mm) further than the other of the first and second forming surfaces, more preferably between about 3 inches (76 mm) and about 5 inches (127 mm) and more preferably about 4 inches (102 mm) and about 5 inches (127 mm). It should be appreciated, however, that speed and distance differentials outside this range can also be used depending on the particular end use and the variance of other parameters such as, for example, the polymers and fibers being used, the deposition rate, the size of the holes in the first forming surface, the dwell time of the web on the forming surfaces, the gap, if any, between the forming surfaces and the amount of vacuum being used to draw the fibers down onto the forming surfaces.

For the uses described herein, the projections will typically have overall heights 35 in the range of about 0.25 millimeters (0.01 inches) to at least about 9 millimeters (0.35 inches), and in some embodiments, from about 0.5 millimeters (0.02 inches) to about 3 millimeters (0.12 inches). Generally speaking, the projections 30 are filled with fibers and thus have desirable resiliency useful for wiping and scrubbing.

Product Applications

One of the advantages of the web 10 according to the present invention is that it has two different aesthetic feels depending on the direction in which the material is contacted or engaged. Because of the uniform orientation of the projections 30, a knap is created on the top surface 12 of the web which is perceptible to human touch and feel. If the material is rubbed or engaged in one direction, it has a rougher feel that if rubbed or engaged in the opposite direction. This is the case when the overhanging edge 64 is the leading edge during the engagement process. Conversely, when the overhanging edge 64 is the trailing edge during the engagement process, the web 10 has a smoother feel.

The fibrous nonwoven web 10 may be used in a wide variety of articles and uses. For example, the web may be incorporated into an "absorbent article" that is capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, mitt wipes, and so forth; medical absorbent articles, such as garments, fenestration materials, underpads, bedpads, bandages, absorbent drapes, and medical wipes; food service wipers; clothing articles; pouches, and so forth. Other applications include facial and cosmetic wipes, both wet and dry, as well as household cleaning wipes both as individual sheets and as disposable attachments for cleaning tools such as mops and other handheld cleaning devices. Materials and processes suitable for forming such articles are well known to those skilled in the art.

Figure 8:
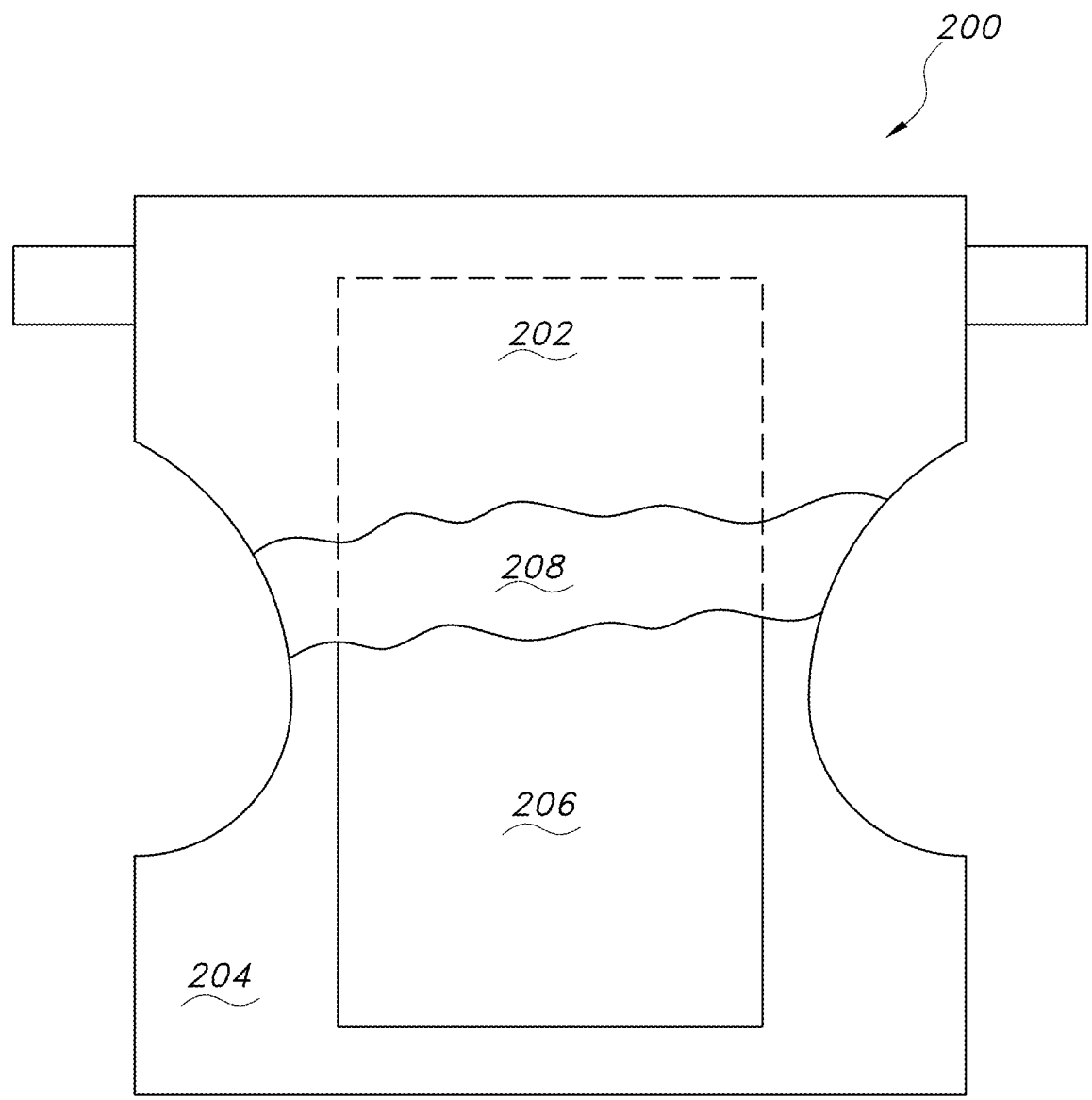
FIG. 8 is a cutaway top plan view of a personal care absorbent article, in this case a diaper, which can employ the fibrous nonwoven web with uniform, directionally-oriented projections according to the present invention.

Personal care absorbent articles typically have certain key components which may employ the web 10 of the present invention. Turning to FIG. 8 there is shown a basic diaper design 200. Typically such products 200 will include a body side liner or skin-contacting material 202, a garment-facing material or sheet also referred to as a backsheet 204 and an absorbent core 206 disposed between the body side liner 202 and the garment facing sheet 204. In addition, it is also common for the product to have an optional layer 208 which is commonly referred to as a surge or transfer layer disposed between the body side liner 202 and the absorbent core 206.

The web 10 according to the present invention may be used as all or a portion of any one or all of these aforementioned components of such personal care products 200 including one of the external surfaces (202 or 204). For example, the web 10 may be used as the body side liner 202 in which case it is more desirable for the projections 30 to be facing outwardly so as to be in a body contacting position in the product 200. The laminate 10 may also be used as the surge or transfer layer 208 or as the absorbent core 206 or a portion of the absorbent core 206. Finally, the web 10 may be used as the outermost side of the garment facing sheet 204 in which case it may be desirable to attach a liquid impervious film or other material (not shown) to the bottom surface 14 of the web 10.

EXAMPLES

In the following examples, Examples 1 and 2 provide specific information regarding two embodiments of the process and fibrous nonwoven web 10 of the invention while Comparative Example 1 describes a similar process and resulting fibrous nonwoven web, but without the directional orientation of the projections. In all three examples, the polymer composition used in the production of the meltblown fibers is the same and is as follows:

85% by weight Metocene MF650X, a propylene homopolymer having a density of 0.91 g/cm$^3$ and melt flow rate of 1200 g/10 minute (230° C., 2.16 kg), which is available from Basell Polyolefins.

15% by weight Vistamaxx 2330, a propylene/ethylene copolymer having a density of 0.868 g/cm$^3$, meltflow rate of 290 g/10 minutes (230° C., 2.16 kg) which is available from ExxonMobil Corp.

Also, in all 3 examples, the pulp fibers were fully treated southern softwood pulp obtained from the Weyerhaeuser Co. of Federal Way, Wash. under the designation "CF-405."

To calculate the differential in distance traveled between the first forming surface 140 and the second forming surface 150 and thus the degree of directional orientation of the projections 30 in the web 10, the difference in travel of the two forming surfaces (140 and 150) must be measured over a prescribed distance. The distance used to make this measurement in the below examples was the distance between a first lay down point 141 on the first forming surface 140 and a second take-up point 145 on the first forming surface 140. See FIG. 3. The location of the first lay down point (first location 141) should be below the central-most set of die tips or other deposition device 172 of the apparatus 170. The location of the take up point (second location (145) is generally the point at which the heads 50 of the projections 30 of the fibrous nonwoven web 10 are no longer in contact with the top surface 152 of the second forming surface 150. As shown in FIG. 3, the distance between first location 141 and second location 145 is referred to as distance "D1". In the time it takes the first forming surface 140 to travel the distance D1, the second forming surface 150 will have traveled a different distance "D2" which may be longer or shorter than D1 depending on the speed of each forming surface. As this is a variable distance depending on the speed differential of the two forming surfaces, D2 is not shown in FIG. 3.

Referring again to FIG. 3 of the drawings, a pair of markers, first marker 141a and second marker 141b, are made on the respective upper forming surface 140 and the lower forming surface 150 at a first location 141 directly below the point of fiber deposition from the apparatus 170. If more than one forming bank is being used, it is desirable to make the point 141 coincide with the forming bank which is furthest from the take-up roll 180. The markers 141a and 141b should be in vertical alignment with one another and the first location 141 marker. The marker for first location 141 should be placed at a stationary location relative to the overall apparatus 130 as should the second location 145 marker as these are the two stationary reference points for the calculations set forth below and the constant distance D1.

Any number of materials may be used to form the markers 141, 141a, 141b and 145 including inks, paints, tapes, mechanical and electronic markers. Depending on the speeds of the forming surfaces (140 and 150), the markers may be visible with the naked eye and changes in the relative position of the markers may be measured with a ruler or similar device. Alternatively, the markers may contain components (such as reflective surfaces or digital/electronic senders or sensors) which can be tracked with electronic, photographic and/or other imaging and sensing devices.

For purposes of demonstrating how to calculate the difference in distance traveled by the two forming surfaces (140 and 150) between first location 141 and second location 145, assume that the first forming surface 140 is moving faster than the second forming surface 150. (The calculation is also valid for the reverse scenario.) As mentioned previously, the distance D1 between first location 141 and second location 145 is a known and set distance. Distance D2 is the distance that the second forming surface 150 will have moved (as tracked by the second marker 141b) in the time "t" that the first forming surface 140 moves distance D1 (that is the time that first marker 141a takes to travel between first location 141 and second location 145). The differential distance "y" that the first forming surface 140 and thus first marker 141a travels as compared to the distance the second forming surface 150 has traveled in the same amount of time "t" is equal to the equation y=D1−D2. Additionally, "S1" is the speed of the first forming surface 140 and "S2" is the speed of the second forming surface 150. Also, t=D1/S1 and t=D2/S2. Therefore, substituting for like values in the foregoing equations:

$$t=(D2/S2)=(D1-y)/S2) \text{ and so:}$$

$$(D1/S1)=[(D1-y)/S2] \text{ and solving for } y \text{ yields:}$$

$$y=D1\times[1-(S2/S1)].$$

As a result, the difference in distance that one forming surface travels versus the other in the process is dependent on both the distance D1 and the ratio of the speeds (S1 and S2) at which the two forming surfaces are traveling. In this regard, "y" will be a positive number when S1 is greater than S2 (that is, first forming surface 140 is traveling faster than second forming surface 150), and "y" will be a negative number when S1 is less than S2 (that is, first forming surface 140 is traveling slower than second forming surface 150). Consequently, the absolute value of "y" should be used.

In view of the above and in view of the examples below, the distance differential "y" as defined herein will typically be between about 2 inches (51 mm) and about six inches (152 mm), alternately between about 3 inches (76 mm) and about 5 inches (127 mm) and still further between about 4 inches (102 mm) and about 5 inches (127 mm).

Example 1

A coform web was formed via a two-bank process in which each bank consisted of two heated streams of meltblown fibers and a single stream of fiberized pulp fibers as described above and shown in FIGS. 3 and 4. Note that in FIG. 3 only a single bank apparatus 170 is shown but for the below examples, two banks were used.

In the first bank (that is, the bank that deposits fibers directly onto the top surface 147 of the first forming surface 140), the polypropylene of each stream was supplied to respective meltblown dies at a rate of 2.73 kg to 2.95 kg of polymer per 2.54 cm of die tip width per hour (5.0 to 5.5 pounds of polymer per inch of die tip width per hour). The meltblown dies were positioned such that the tips were 25.4 cm (10 inches) horizontally from the pulp nozzle centerline and 25.4 cm (10 inches) above the first forming surface 140. They were tilted inwardly towards the pulp nozzle at an angle of 80° from the horizontal. The pulp nozzle was 15.24 cm (6 inches) above the first forming surface. The pulp was delivered at a rate of 6.4 kg per 2.54 cm of pulp nozzle width per hour (14 pounds per inch of pulp nozzle width per hour).

In the second bank (that is, the bank that deposits fibers on top of the web formed by the first bank), the polypropylene of each stream was supplied to respective meltblown dies at a rate of 2.27 kg of polymer per 2.54 cm of die tip width per hour (5.0 pounds of polymer per inch of die tip width per hour). The meltblown dies were positioned such that the tips were 17.8 cm (7 inches) horizontally from the pulp nozzle centerline and 17.8 cm (7 inches) above the first forming surface 140. They were tilted inwardly towards the pulp nozzle at an angle of 50° from the horizontal. The pulp nozzle was 24.1 cm (9.5 inches) above the first forming surface 140. The pulp was delivered at a rate of 2.3 kg per 2.54 cm of pulp nozzle width per hour (5 pounds per inch of pulp nozzle width per hour).

Figure 5:
FIG. 5 is a photo of a cross-sectional view of the material according to the present invention described in Example 1.

In total, the resulting fibrous web had a meltblown fiber content of about 52% and a pulp fiber content of about 48% on a weight percent basis. The second forming surface 150 was an ELECTRATECH™ 56 (Albany International Co.) forming wire. To create the projections 30, the first forming surface 140 was a rubber mat having a thickness of approximately 2.65 millimeters (0.10 inch) and containing 6.35 mm (0.25 inch) diameter circular holes 142 arranged in a pattern similar to that shown in FIG. 4 of the drawings. The spacing of the holes 142 was 9.53 mm (0.375 inches) from center to center in both the machine and cross directions. A vacuum box 160 was positioned below the second forming surface 150 to aid in deposition of the fibers and the formation of the web and was set to a vacuum level sufficient to draw the fibrous mixture from the first bank into the holes 142 in the first forming surface 140. The vacuum level was also sufficient to draw a portion of the fibers that entered the holes 142 of the first forming surface 140 into contact with the second forming surface 150. The second forming surface 150 was driven by a drive roll (one of the four rolls 156). The first forming surface 140 was driven by contact with the second forming surface 150 and was not driven independently of the second forming surface 150. To create the directional orientation of the projections 30, the first forming surface 140 was run at a first speed of 195 meters per minute (640 feet per minute) and the second forming surface 150 was run at a second speed of approximately 194 meters per minute (637 feet per minute). The speed mismatch between the first and second forming surfaces resulted in the first forming surface 140 traveling 5.1 cm (2 inches) farther than the second forming surface 150 over the distance "D1" of 12.2 m (40 feet). Thus the distance differential value "y" was equal to 51 millimeter. The resultant coform web 10 had a configuration similar to that shown in FIG. 1. A photographic, cross-sectional side view of the web is shown in FIG. 5.

Example 2

A coform web was formed via a two-bank process in which each bank consisted of two heated streams of meltblown fibers and a single stream of fiberized pulp fibers as described above with respect to Example 1.

In the first bank (that is, the bank that deposits fibers directly onto the top surface 147 of the first forming surface 140), the polypropylene of each stream was supplied to respective meltblown dies at a rate of 2.73 kg to 2.95 kg of polymer per 2.54 cm of die tip width per hour (6.0 to 6.5 pounds of polymer per inch of die tip width per hour). The meltblown dies were positioned such that the tips were 25.4 cm (10 inches) horizontally from the pulp nozzle centerline and 25.4 cm (10 inches) above the first forming surface 140. They were tilted inwardly towards the pulp nozzle at an angle of 80° from the horizontal. The pulp nozzle was 15.2 cm (6 inches) above the first forming surface 140. The pulp was delivered at a rate of 13.6 kg per 2.54 cm of pulp nozzle width per hour (30 pounds per inch of pulp nozzle width per hour).

In the second bank (that is, the bank that deposits fibers on top of the web formed by the first bank), the polypropylene of each stream was supplied to respective meltblown dies at a rate of 2.3 kg of polymer per 2.54 cm of die tip width per hour (5.0 pounds of polymer per inch of die tip width per hour). The meltblown dies were positioned such that the tips were 17.8 cm (7 inches) horizontally from the pulp nozzle centerline and 17.8 cm (7 inches) above the first forming surface 140. They were tilted inwardly towards the pulp nozzle at an angle of 50° from the horizontal. The pulp nozzle was 24.1 cm (9.5 inches) above the first forming surface 140. The pulp was delivered at a rate of 2.3 kg per 2.54 cm of pulp nozzle width per hours (5 pounds per inch of pulp nozzle width per hour).

In total, the resulting fibrous web had a meltblown fiber content of about 39% and a pulp fiber content of about 61% on a weight percent basis. To create the directional orientation of the projections 30, the first forming surface 140 was run at a first speed of 285 meters per minute (935 feet per minute) and the second forming surface 150 was run at a second speed of approximately 281 meters per minute (923 feet per minute). The speed mismatch between the first and second forming surfaces resulted in the first forming surface 140 traveling 15.2 cm (6"-inches) farther than the second forming surface 150 over the distance "D1" of 12.2 m (40 feet). Thus the distance differential value "y" was equal to 152 millimeter.

Figure 6:
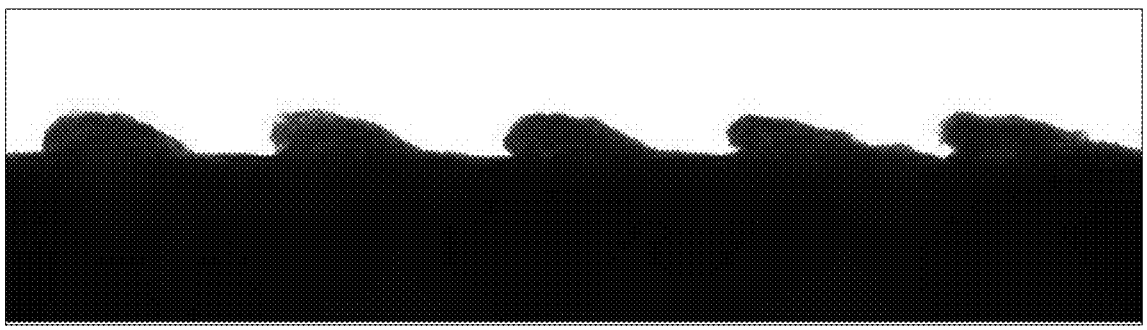
FIG. 6 is a photo of a cross-sectional view of the material according to the present invention described in Example 2.

The resultant coform web 10 had a configuration similar to that shown in FIG. 1. A photographic, cross-sectional side view of the web is shown in FIG. 6.

Comparative Example 1

Comparative example 1 was run with no speed differential between the first forming surface 140 and the second forming surface 150. The first and second forming surfaces were driven independently, but at the same speed of approximately 195 meters per minute (640 feet per minute). As a result, no directional orientation of the projections was achieved and no overhang area was created. Further, the distance differential value "y" was equal to 0 millimeter due to their being no speed differential between the two forming surfaces.

A coform web was formed via a two-bank process in which each bank consisted of two heated streams of meltblown fibers and a single stream of fiberized pulp fibers as described above and shown in FIGS. 3 and 4. The forming conditions and delivery rates for the meltblown fibers and pulp were the same as in Example 1 resulting in. a fibrous web with a meltblown fiber content of about 52% and a pulp fiber content of about 48% on a weight percent basis. A photographic, cross-sectional side view of the web is shown in FIG. 7.

Figure 7:
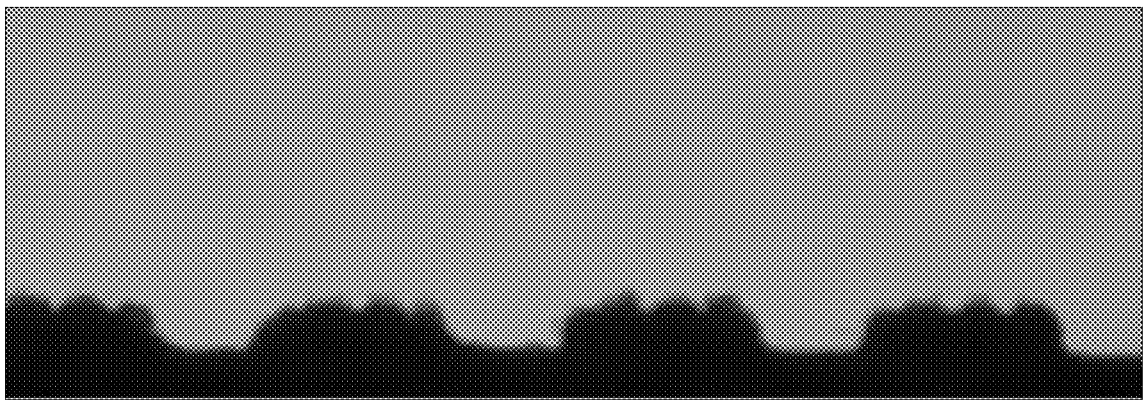
FIG. 7 is a photo of a cross-sectional view of the material described in Comparative Example 1.

As can be seen from FIGS. 5, 6 and 7, due to the speed differential and thus the difference in the distance traveled by the first forming surface 140 versus the second forming surface 150, a series of uniform, directionally-oriented projections 30 could be formed in the fibrous nonwoven web 10. See FIGS. 5 an 6. Without the speed differential and/or insufficient contact between the head portions 50 of the projections 30 with the top surface 152 of the second forming surface 150, no directional orientation occurs. Also it can be seen in comparing the materials of FIGS. 5 and 6 that with increased speed differential and travel distance differential of the two forming surfaces between fiber laydown and web take-up (Example 2 as compared to Example 1), greater directional orientation and overhang can be achieved with respect to the projections 30.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A process for forming a fibrous nonwoven web with uniform, directionally-oriented projections comprising:
   providing a first forming surface defining a plurality of openings therein;
   providing a second forming surface which is pervious to air;
   overlaying said first forming surface atop said second forming surface;
   causing said first forming surface to travel in a first direction at a first speed;
   causing said second forming surface to travel in said first direction at a second speed to cause a speed differential between said first forming surface and said second forming surface;
   depositing a plurality of fibers onto said first forming surface to form a fibrous nonwoven web;
   causing a portion of said plurality of fibers to extend through said openings in said first forming surface and contact said second forming surface to form a plurality of fibrous projections in said fibrous nonwoven web; said speed differential causing said projections to have a uniform, directional orientation relative to said first direction of travel of said first forming surface and each projection having a base portion formed of fibers throughout its cross section and a head portion connected to said base portion and wherein said head portion is skewed relative to said base portion thereby forming an overhang; and
   removing said fibrous nonwoven web with said uniform, directionally-oriented projections from said first forming surface.

2. The process of claim 1 which further includes providing a vacuum source beneath said second forming surface on a side of said second forming surface opposite said first forming surface to aid in a movement of said fibers through said openings in said first forming surface and contact said second forming surface.

3. The process of claim 1 which further includes causing said first and second forming surfaces to travel at a distance differential "y" as defined herein of between about 51millimeters (2 inches) and about 152 millimeters (6 inches).

4. The process of claim 1 which further includes driving one of said first and second forming surfaces by frictional engagement with the other of said first and second forming surfaces.

5. The process of claim 1 which further includes driving said first forming surface in said first direction independently of said second forming surface.

6. A process for forming a fibrous nonwoven web with uniform, directionally-oriented projections comprising:
   providing a first forming surface defining a plurality of openings therein;
   providing a second forming surface which is pervious to air;
   overlaying said first forming surface atop said second forming surface;
   causing said first forming surface to travel in a first direction at a first speed;
   causing said second forming surface to travel in said first direction at a second speed to cause a speed differential between said first forming surface and said second forming surface;

depositing a plurality of fibers onto said first forming surface to form a fibrous nonwoven web;

causing a portion of said plurality of fibers to extend through said openings in said first forming surface and contact said second forming surface to form a plurality of fibrous projections in said fibrous nonwoven web; said speed differential causing said projections to have a uniform, directional orientation relative to said first direction of travel of said first forming surface and each projection having a solid base portion formed of fibers throughout its cross section and a head portion connected to said base portion and wherein said head portion is skewed relative to said base portion thereby forming an overhang.

7. The process of claim 6 which further includes providing a vacuum source beneath said second forming surface on a side of said second forming surface opposite said first forming surface to aid in a movement of said fibers through said openings in said first forming surface and contact said second forming surface.

8. The process of claim 6 which further includes causing said first and second forming surfaces to travel at a distance differential "y" as defined herein of between about 51 millimeters (2 inches) and about 152 millimeters (6 inches).

9. The process of claim 6 which further includes driving one of said first and second forming surfaces by frictional engagement with the other of said first and second forming surfaces.

10. The process of claim 6 which further includes driving said first forming surface in said first direction independently of said second forming surface.

11. A process for forming a fibrous nonwoven web with uniform, directionally-oriented projections comprising:

providing a first forming surface defining a plurality of openings therein;

providing a second forming surface which is pervious to air;

overlaying said first forming surface atop said second forming surface;

causing said first forming surface to travel in a first direction at a first speed;

causing said second forming surface to travel in said first direction at a second speed to cause a speed differential between said first forming surface and said second forming surface;

depositing a plurality of fibers onto said first forming surface to form a fibrous nonwoven web;

causing a portion of said plurality of fibers to extend through said openings in said first forming surface and contact said second forming surface to form a plurality of fibrous projections in said fibrous nonwoven web; said speed differential causing said projections to have a uniform, directional orientation relative to said first direction of travel of said first forming surface and each projection having a base portion and a head portion connected to said base portion, said head portion is skewed relative to said base portion thereby forming an overhang and wherein said base portion has a base portion width and said head portion has a head portion width greater than the base portion width.

12. The process of claim 11, wherein the base portion is formed of fibers throughout its cross section.

* * * * *